United States Patent [19]
Luo et al.

[11] Patent Number: 6,114,111
[45] Date of Patent: Sep. 5, 2000

[54] MAMMALIAN PROTEIN INTERACTION CLONING SYSTEM

[75] Inventors: Ying Luo, Los Altos; Betty Huang, San Leandro; Donald Payan, Hillsborough, all of Calif.

[73] Assignee: Rigel Pharmaceuticals, Inc., Sunnyvale, Calif.

[21] Appl. No.: 09/050,863

[22] Filed: Mar. 30, 1998

[51] Int. Cl.[7] ................................................... C12Q 1/70
[52] U.S. Cl. .............................. 435/5; 435/455; 435/456; 435/457; 435/458; 435/465; 435/235.1; 435/236; 435/325; 435/320.1
[58] Field of Search .................... 435/69.1, 455, 435/456, 457, 458, 465, 466, 467, 235.1, 236, 325, 320.1, 5

[56] References Cited

U.S. PATENT DOCUMENTS

| | | | |
|---|---|---|---|
| 5,139,941 | 8/1992 | Muzyczka et al. | 435/172.3 |
| 5,283,173 | 2/1994 | Fields et al. | 435/6 |
| 5,468,614 | 11/1995 | Fields et al. | 435/6 |
| 5,525,490 | 6/1996 | Erickson et al. | 435/29 |
| 5,637,463 | 6/1997 | Dalton et al. | 435/6 |
| 5,667,973 | 9/1997 | Fields et al. | 435/6 |

FOREIGN PATENT DOCUMENTS

97/31113  8/1997  WIPO.

OTHER PUBLICATIONS

Fields and Song, "A novel genetic system to detect protein–protein interactions," *Nature*, 340: 245–246 (Jul. 1989).

Fearon et al., "Karyoplasmic interaction selection strategy: A general strategy to detect protein–protein interactions in mammalian cells," *Proc. Natl. Acad. Sci. USA*, 89:7958–7962 (Sep. 1992).

Dang et al., "Intracellular Leucine Zipper Interactions Suggest c–Myc Hetero–Oligomerization," *Molecular and Cellular Biology*, 1(2):954–962 (Feb. 1991).

Chien et al., "The two–hybrid system: A method to identify and clone genes for proteins that interact with a protein of interest," *Proc. Natl. Acad. Sci. USA*, 88:9578–9582 (Nov. 1991).

Vasavada et al., "A contingent replication assay for the detection of protein–protein interactions in animal cells," *Proc. Natl. Acad. Sci. USA* 88:10686–10690 (Dec. 1991).

Luo et al., *Biotechniques* 22(2): 350–352, Feb. 1997.

Richardson et al., *J. Virology* 65(6):3122–3130, Jun. 1991.

*Primary Examiner*—Robert D. Budens
*Attorney, Agent, or Firm*—Flehr Hohbach Test Albritton and Herbert LLP; Robin M. Silva

[57] ABSTRACT

The present invention is directed to compositions and methods for a genetic system of detecting protein—protein interactions in a mammalian host cell. Two fusion proteins are made in the host cell. The first fusion protein contains a DNA binding domain which is fused to a so-called bait protein. The second fusion protein consists of a transcriptional activation domain fused to a so-called test protein. The transcriptional activation domain is recruited to the promoter through the functional interaction between the bait protein and the test protein. Subsequently the transcriptional activation domain interacts with the basal transcription machinery to activate expression of one or more reporter genes which can be identified and characterized. The individual compositions are useful for analyzing protein—protein interactions between known proteins and to isolate, clone and characterize unknown proteins. The individual compositions can be used to express the fusion proteins either transiently or stably.

41 Claims, 4 Drawing Sheets

MAMMALIAN PROTEIN INTERACTION CLONING SYSTEM

FIELD OF THE INVENTION

The present invention is directed to compositions and methods for a genetic system of detecting protein—protein interactions in a mammalian host cell. The protein interactions are detected by using fusion proteins whose expression and interaction with each other results in transcriptional activation.

BACKGROUND OF THE INVENTION

Protein—protein interactions are of paramount and fundamental interest in biological systems. These interactions are involved in a wide variety of important biological reactions, including the assembly of enzyme subunits, in antigen-antibody reactions, in supramolecular structures of ribosomes, filaments, and viruses, in recognition and transport, in transcription regulation, and in ligand-receptor interactions. In addition, the area of protein—protein interactions has received significant attention in the area of signal transduction and biochemical pathway analysis.

Traditionally, protein—protein interactions were evaluated using biochemical techniques, including chemical cross-linking, co-immunoprecipitation and co-fractionation and -purification. Recently genetic systems have been described to detect protein—protein interactions. The first work was done in yeast systems, and was termed the "yeast two-hybrid" system. The basic system requires a protein—protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463.

However, while the yeast system works well, it is unsuitable for use in mammalian systems for a variety of reasons. Furthermore, the existing mammalian two-hybrid systems are neither suitable for a wide variety of cells, nor flexible, as they generally require quite highly specialized conditions. In addition, the existing mammalian two-hybrid systems are generally transient systems, rather than stable systems. Finally, these systems tend to have high background signals from non-specific interactions, giving rise to "false positives".

A number of factors make a flexible mammalian two-hybrid system highly desirable. First of all, post-translational modifications of proteins may contribute significantly to their ability to interact, yet mammalian cells have different post-translational modification systems than yeast. Thus, proteins that interact in a yeast system may not interact with the same specificity or avidity when placed in a mammalian cell. Similarly, proteins that would interact with correct post-translational processing may not be identified in a yeast system. In addition, a mammalian two-hybrid system that could be used in a wide variety of mammalian cell types would be highly desirable, since the regulation, induction, processing, etc. of specific proteins within a particular cell type can vary significantly; it would thus be a distinct advantage to assay for relevant protein—protein interactions in the relevant cell type. For example, proteins involved in a disease state could be tested in the relevant disease cells, resulting in a higher chance of identifying important protein interactions. Similarly, for testing of random proteins, assaying them under the relevant cellular conditions will give the highest chance of positive results. Furthermore, the mammalian cells can be tested under a variety of experimental conditions that may affect intracellular protein—protein interactions, such as in the presence of hormones, drugs, growth factors and cytokines, cellular and chemical stimuli, etc., that may contribute to conditions which can effect protein—protein interactions.

Thus, a robust and adaptable mammalian two-hybrid system which can work in a wide variety of mammalian cell types is highly desirable.

Accordingly, it is an object of the invention to provide compositions and methods useful in a two-hybrid system which can be utilized reproducibly and stably in mammalian cells.

SUMMARY OF THE INVENTION

The invention provides compositions and methods useful in a mammalian two hybrid system for the detection of protein—protein interactions.

In one aspect of the invention, the invention provides compositions comprising a bait vector and a test vector. The bait vector comprises a first selection gene, a bait vector viral origin of replication which requires a bound viral replication protein to effect replication, and a first fusion gene. The fusion gene comprises a first sequence encoding a nucleic acid binding domain, and a second sequence comprising either a cloning sequence comprising a cloning site, or a sequence encoding a bait protein. The test vector comprises a second selection gene, a test vector viral origin of replication which requires a bound viral replication protein to effect replication, and a second fusion gene. The second fusion gene comprises a third sequence encoding a transcriptional activation domain, and a fourth sequence comprising either a cloning sequence comprising a cloning site or a sequence encoding a test protein.

In a further aspect, the compositions further comprise a reporter vector comprising a first detectable gene, a viral replication protein gene, and an operator site, which upon binding of the nucleic acid binding domain and the transcriptional activation domain due to a protein—protein interaction of the bait protein and the test protein, will activate transcription of the first detectable gene and the viral replication protein gene.

In a further aspect, the invention provides compositions comprising a retroviral bait vector comprising a first fusion gene and an optional selection gene, and a retroviral test vector comprising a second fusion gene and an optional selection gene. The composition may further comprise a retroviral reporter vector comprising a first detectable gene and an operator site.

In an additional aspect, the invention provides mammalian host cells containing the compositions of the invention.

In a further aspect, the invention provides methods for detecting an interaction between a bait protein and a test protein comprising providing a mammalian host cell containing a bait vector, a test vector, and a reporter vector, which may or may not be retroviral vectors. The host cell is subjected to conditions under which the first fusion gene and the second fusion gene are expressed to produce a first fusion protein and a second fusion protein. The method further comprises determining whether a protein—protein interaction between the first fusion protein and the second fusion protein occurred.

DETAILED DESCRIPTION OF THE INVENTION

As outlined herein, the present invention is directed to compositions and methods useful as a mammalian two-hybrid system. While the basic mechanism is similar to the yeast two hybrid system based on transcription activation, the present invention can be used in any number of mammalian cells, is highly stable, and is designed to reduce the background signals frequently found in other systems. The present invention thus provides a robust and versatile system to evaluate protein—protein interactions in a wide variety of mammalian cells under any number of different conditions.

Briefly, transcription can be activated through the use of two functional domains of a transcription activator protein; a domain or sequence of amino acids that recognizes and binds to a nucleic acid sequence, i.e. a nucleic acid binding domain, and a domain or sequence of amino acids that will activate transcription when brought into proximity to the target sequence. Thus the transcriptional activation domain is thought to function by contacting other proteins required in transcription, essentially bringing in the machinery of transcription. It must be localized at the target gene by the nucleic acid binding domain, which putatively functions by positioning the transcriptional activation domain at the transcriptional complex of the target gene.

These two domains can be either from the same transcriptional activator protein, or can be from different proteins (see McKnight et al., PNAS USA 89:7061 (1987); Ghosh et al., J. Mol. Biol. 234(3):610–619 (1993); and Curran et al., 55:395 (1988)). A variety of transcriptional activator proteins comprising an activation domain and a binding domain are known in the art, as is described below.

Thus, in the two-hybrid system, a first protein, or "bait protein", as termed herein, is fused to a nucleic acid binding domain of a nucleic acid binding protein, such as a transcriptional activator protein, and a second protein, or "test protein", is fused to the activator domain of a transcriptional activator. If the bait protein and the test protein bind, i.e. have a specific protein—protein interaction, the activator domain is brought into position near the nucleic acid binding domain, and transcription of a detectable gene occurs. If there is little or no interaction, there little or is no detectable protein made.

The invention is generally described as follows. In the preferred embodiment of the present invention, the mammalian two-hybrid system comprises three components: a bait vector, a test vector, and a reporter vector. The bait vector has a viral origin of replication that requires the presence of a viral replication protein to effect replication, a selection gene, and a first fusion construct comprising a nucleic acid binding domain from a transcriptional activator protein fused to a "bait" protein; that is, a protein for which a protein—protein interaction is sought. The test vector also has a viral origin of replication which requires a viral replication protein and a selection gene, and further comprises a second fusion construct comprising a transcriptional activation domain fused to a "test" protein. The reporter construct comprises a detectable gene, a viral replication protein gene, and a regulatory site such as an operator. Upon binding of the nucleic acid binding domain and the transcriptional activation domain, due to a protein—protein interaction of the bait and test proteins, the operator is activated and will cause increased transcription of the detectable gene and the viral replication protein gene. The viral replication protein can then bind to the viral origin of replication on the bait and test vectors to permit replication of the vector, ensuring survival of the cell due to the selection gene. The detectable or reporter gene then serves as the basis of a sorting or screening system to isolate cells which have a protein—protein interaction, and the test protein may be identified and characterized as desired.

Accordingly, the present invention provides compositions comprising three components: a bait vector, a test vector, and a reporter vector. By "vector" or "episome" herein is meant a replicon used for the transformation of host cells. The vectors may be either self-replicating extrachromosomal vectors ("plasmids") or vectors which integrate into a host genome. A preferred embodiment utilizes retroviral vectors, as is more fully described below.

For non-retroviral embodiments, suitable vectors are derived from any number of known vectors, including, but not limited to, pCEP4 (Invitrogen), pCI-NEO (Promega), and pBI-EGFP (Clontech). Basically, any mammalian expression vectors with strong promoters such as CMV can be used to construct test or bait vectors.

Generally, these expression vectors include transcriptional and translational regulatory nucleic acid operably linked to nucleic acids which are to be expressed. "Operably linked" in this context means that the transcriptional and translational regulatory nucleic acid is positioned relative to any coding sequences in such a manner that transcription is initiated.

Generally, this will mean that the promoter and transcriptional initiation or start sequences are positioned 5' to the coding region. The transcriptional and translational regulatory nucleic acid will generally be appropriate to the host cell used, as will be appreciated by those in the art. Numerous types of appropriate expression vectors, and suitable regulatory sequences, are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters, hybrid or synthetic promoters. Hybrid promoters, which combine elements of more than one promoter, are also known in the art, and are useful in the present invention.

In general, the vectors of the present invention utilize two different types of promoters. In a preferred embodiment, the promoters on the bait and test vectors are constitutive, and drive the expression of the fusion proteins and selection genes, if applicable, at a high level. However, it is possible to utilize inducible promoters for the fusion constructs and selection genes, if necessary, for example if toxic proteins are used as either the bait or test proteins.

Preferred promoters for driving expression of the fusion constructs, and the selection genes, if applicable, on the bait and test vectors, include, but are not limited to, cytomegloviral promoters (CMV), SV40, SRα (Takebe et al., Mole. Cell. Biol. 8:466 (1988)), respiratory synsitial viral promoters (RSV), thymine kinase (TK), β-globin, etc. Particularly preferred promoters are CMV promoters. Preferred retroviral promoters are discussed below.

In a preferred embodiment, the promoter on the reporter vector is associated with at least copy of the bait fusion protein binding site, such as an operator as defined below, and is essentially an inducible promoter. Induction in this case comprises a protein—protein interaction of the bait and test proteins sufficient to cause the association of the nucleic acid binding domain and the transcriptional activator domain resulting in transcription activation. What is important is that the promoter-operator system (i.e. the minimal promoter) on the reporter construct does not result in transcription unless the protein—protein interaction is present, although as will be appreciated by those in the art, there may be some low level of background constitutive expression.

In addition, the expression vector may comprise additional elements such as a viral origin of replication, selection genes, etc., as is more fully described below. In addition, for integrating expression vectors (non-retroviral), the expression vector generally contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art. As for all of the vectors described herein, the vector may be extrachromosomal, or may be integrated into the genome of the host cell. In a preferred embodiment, one or more of the vectors may contain a RNA splicing sequence upstream or downstream of the test or bait protein gene to increase the level of gene expression. See Barret et al., Nucleic Acids Res. 1991; Groos et al., Mole. Cell. Biol. 1987; and Budiman et al., Mole. Cell. Biol. 1988.

In a preferred embodiment, either the vector particularly the test vector) or one or both of the fusion constructs may contain a "rescue" sequence. A rescue sequence is a sequence (either nucleic acid or amino acid) which may be used to purify or isolate either the test or bait proteins or the nucleic acid encoding them. Thus, for example, protein rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, one or more retroviral vectors are used. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins—gag, pol, and env— that are required for packaging, processing, reverse transcription, and integration of recombinant genomes. Those RNA molecules that have in cis the ψ packaging signal are packaged into maturing virions.

Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express. In addition, transfection efficiencies can be extremely high, thus obviating the need for selection genes in some cases.

A particularly well suited retroviral transfection system is described in Mann et al., supra: Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); WO 94/19478; PCT US97/01019, and references cited therein, all of which are incorporated by reference.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing fusion constructs at uniformly high levels; and promoters driving expression of a second gene, placed in sense or anti-sense relative to the 5' LTR.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE (see PCT US97/01019, incorporated by reference).

As for the other vectors, the retroviral vectors may include inducible and constitutive promoters. Constitutive promoters are preferred for the bait and test vectors, and include, but are not limited to, CMV, SV40, Srα, RSV, and TK. Similarly, the reporter vector promoter is associated with at least one copy of an operator, as outlined herein.

In addition, it is possible to configure a retroviral vector to allow expression of bait genes or test genes after integration of a bait or test vector in target cells. For example, Tet-inducible retroviruses can be used to express bait or test genes (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In general, three types of vectors are used in the present invention. The first is a bait vector, generally comprising a first selection gene, a viral origin of replication which requires a bound viral replication protein to effect replication, and a first fusion gene.

Selection genes allow the selection of transformed host cells containing the vector, and particularly in the case of mammalian cells, ensures the stability of the vector, since cells which do not contain the vector will generally die. Selection genes are well known in the art and will vary with the host cell used. Suitable selection genes include, but are not limited to, neomycin, blastocidin, bleomycin, puromycin, hygromycin, and other drug resistance genes. In some cases, for example when using retroviral vectors, the requirement for selection genes is lessened due to the high transformation efficiencies which can be achieved. Accordingly, selection genes need not be used in retroviral constructs, although they can be. In addition, when retroviral vectors are used, the bait and test vectors may also contain detectable genes as are described below rather than selection genes; it may be desirable to verify that the vector is present in the cell, but not require selective pressure for maintenance.

In one embodiment, the bait vector also comprises a viral origin of replication which requires a bound viral replication protein to effect replication. As is known in the art, the only extrachromosomal vectors which replicate in mammalian cells are virally derived. A number of viral origin of replications require the binding of a specific viral replication protein to effect replication. Suitable origin of replication/viral replication protein pairs include, but are not limited to, the Epstein Barr origin of replication (SEQ ID NO: 1) and the Epstein Barr nuclear antigen (SEQ ID NO:2; see Sugden et al., Mole. Cell. Biol. 5(2):410–413 (1985)); the SV40 origin of replication (SEQ ID NO:3) and the SV40 T antigen (SEQ ID NO:4; see Margolskee et al., Mole. Cell. Biol. 8(7):2837 (1988)). The bait vector origin of replication and the test vector origin of replication are preferably the same, but as will be appreciated in the art, can be different.

As is described herein, the coding sequence for the viral replication protein can be on the reporter construct, or on either of the bait or test vectors, or both. In a preferred embodiment, the coding sequence for the viral replication protein is on the reporter construct, as this will serve to decrease the background signal and false positives. This serves as a second reporter gene, effectively, as the plasmids are not replicated unless the bait protein and the test protein interact sufficiently to cause transcription of the viral replication protein; it is a selection, of sorts, since the lack of one or the other of the bait and test vectors will generally be fatal to the cell, due to the loss of the selection gene. In an alternate embodiment, the viral replication protein coding sequence may be contained on either or both of the bait vector and the test vector, for instance when false positives are not a concern, when the reporter carries another drug selection to ensure its stable integration into the cell, or when an additional reporter gene is desirable. That is, if the viral replication protein is on the bait and/or test vectors, another reporter gene such as luciferase can be used in addition to the first reporter gene.

In addition, the bait vector comprises a first fusion gene. By "fusion gene" or "fusion construct" herein is meant nucleic acid that comprises at least two functionally distinct sequences; i.e. generally sequences from two different genes. As will be appreciated by those in the art, in some embodiments the sequences described herein may be DNA, for example when extrachromosomal plasmids are the vectors, or RNA, for example when retroviral vectors are used. Generally, the sequences are directly linked together without any linking sequences, although in some embodiments linkers such as restriction endonuclease cloning sites or linkers encoding flexible amino acids such as glycine and serine linkers such as are known in the art are used. In a preferred embodiment, the first fusion gene comprises a first sequence encoding a nucleic acid binding domain, and the second sequence encodes a bait protein. By "nucleic acid binding domain" herein is meant a proteinaceous domain which is able to bind a specific nucleic acid sequence, generally a DNA sequence. As noted above, transcriptional activation proteins generally contain at least two domains, a nucleic acid binding domain and a transcriptional activation domain; for the purposes of the present invention, the nucleic acid binding domain and the transcriptional activation domain may come from the same protein or different proteins. As will be appreciated by those in the art, what is important is that the transcriptional activator from which these sequences are derived have functionally distinct domains. Suitable nucleic acid binding domains include, but are not limited to, nucleic acid binding domains from Tet, GAL4 (amino acids 1–147; Fields et al., supra; see also Gill et al., PNAS USA 87:2127 (1990); Chasman et al., Mol. Cell. Biol. 9:4746 (1989)); LexA (Thliveris et al., Proc. Natl. Acad. Sci. 1992; Hurstels et al., EMBO 1986); GCN4 from *S. cerevisiae* (Hope et al., Cell 46:885 (1986); ARD1 from *S. cerevisiae* (Thukral et al., Mol. Cell. Biol. 9:2360 (1989), the human estrogen receptor (Kumar et al., Cell 51:941 (1987), and NF-kB p65, and p53, and derivatives thereof which are functionally similar.

In a preferred embodiment, the first fusion gene further comprises a second sequence encoding a bait protein. "Protein" in this context includes peptides, oligopeptides and proteins. By "bait protein" herein is meant a protein which is to be tested for interaction with another protein. Generally, the bait protein comprises all or part of a target molecule which has either been implicated in a biological process of interest or for which the function is sought. Suitable bait proteins include functional domains of a wide variety of proteins, including, but not limited to, receptors, ligands, protein hormones, enzymes (particularly proteases), antibodies, antigens, nucleic acid processing proteins, transcription proteins, etc. In addition, the bait protein may also be a random protein, for example of from about 2 amino acids to about 100 amino acids, with from about 10 to about 50 amino acids being preferred. In one embodiment, the bait protein is fully randomized, with no sequence preferences or constants at any position. In a preferred embodiment, the protein is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, or to reduce the chance of creation of a stop codon, etc.

In a preferred embodiment, the bias is towards peptides or nucleic acids that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of test proteins as well.

Customarily one bait protein is used to test a library of test sequences as is described below; however, as will be appreciated by those in the art, the bait protein may be one of a library as well, thus forming an experimental matrix wherein two libraries (although the coding regions of the libraries could be identical) are evaluated for protein—protein interactions. In a preferred embodiment, self-activating bait proteins are filtered out from the bait protein library.

In a preferred embodiment, for example when the compositions are to be used in kits, the first fusion gene comprises a first sequence encoding a nucleic acid binding domain and a cloning sequence comprising a cloning site for insertion of nucleic acid encoding a bait protein. In this embodiment, the end user of the kit will add the bait and test proteins to the vectors, depending on their needs and particular targets. Suitable cloning sites are well known in the art.

The present invention also provides test vectors. Generally, the test vector is a distinct vector from the bait and reporter vectors, although as will be appreciated by those in the art, one, two or three independent vectors may be used. That is, the components of the bait and test vectors could reside on a single vector or on two vectors. Similarly, the reporter vector can be independent or part of either the bait or test vector, or the entire system may reside on a single vector, if the size of the vector is not a concern. Generally, when the test protein is a member of a library, as is outlined below, the test vector will be separate from the bait and reporter vectors.

The test vector also generally comprises a selection gene, although as outlined above, this may not be necessary in some embodiments, for example if the test vector is a retroviral vector, or if the test vector is combined with another vector. Preferably, when the bait and test vectors are distinct, the selection gene of the test vector is different from the selection gene of the bait vector, to ensure that both vectors are maintained within the cell. However, in some embodiments this may not be required; accordingly, the first and second selection genes may be the same or different. The test vector also comprises a viral origin of replication, as described above.

The test vector further comprises a second fusion gene comprising a third sequence encoding a transcriptional activator domain and a fourth sequence encoding a test protein. As above, these may be fused directly or via a linker. By "transcriptional activator domain" herein is meant a proteinaceous domain which is able to activate transcription.

Suitable transcription activator domains include, but are not limited to, transcriptional activator domains from GAL4, GCN4, ARD1, the human estrogen receptor, VP16 (Triezenberg et al., Genes Dev. 2(6):718–729 (1988)), and B42 (Gyuris et al, Cell 1993), and NF-kB p65, and derivatives thereof which are functionally similar.

The fourth sequence encodes a test protein. By "test protein" herein is meant a candidate protein which is to be tested for interaction with a bait protein. Protein in this context means proteins, oligopeptides, and peptides, i.e. at least two amino acids attached. In a preferred embodiment, the test protein sequence is one of a library of test protein sequences; that is, a library of test proteins is tested for binding to one or more bait proteins. The test protein sequences can be derived from genomic DNA, cDNA or can be random sequences. Alternatively, specific classes of test proteins may be tested. The library of test proteins or sequences encoding test proteins are incorporated into a library of test vectors, each or most containing a different test protein sequence.

In a preferred embodiment, the test protein sequences are derived from genomic DNA sequences. Generally, as will be appreciated by those in the art, genomic digests are cloned into test vectors. The genomic library may be a complete library, or it may be fractionated or enriched as will be appreciated by those in the art.

In a preferred embodiment, the test protein sequences are derived from cDNA libraries. A cDNA library from any number of different cells may be used, and cloned into test vectors. As above, the cDNA library may be a complete library, or it may be fractionated or enriched in a number of ways.

In a preferred embodiment, the test protein sequences are random sequences. Generally, these will be generated from chemically synthesized oligonucleotides. Generally, random test proteins range in size from about 2 amino acids to about 100 amino acids, with from about 10 to about 50 amino acids being preferred. As above, fully random or "biased" random proteins may be used.

As above, in some embodiments the second fusion gene comprises a third sequence encoding a transcriptional activator domain and a cloning sequence comprising a cloning site for insertion of nucleic acid encoding a test protein.

The present invention also provides reporter vectors. In a preferred embodiment, the reporter vector comprises an operator site, a first detectable gene and a viral replication protein gene.

By "operator" herein is meant a nucleic acid sequence, generally DNA, which will bind the nucleic acid binding domain of the first fusion protein, and, in the presence of the transcriptional activation domain, will activate transcription and cause expression of the detectable gene(s) and viral replication protein gene, if present. As is described herein, the operator is activated when a protein—protein interaction of the bait and test proteins causes the nucleic acid binding domain and the transcriptional activation domain to be in sufficient proximity.

In a preferred embodiment, the nucleic acid sequence (the "binding sequence" or "binding site") which binds the nucleic acid binding domain is repeated within the operator. Thus, an operator preferably has at least one binding site, with at least about 3 binding sites being preferred, and at least about 5 being especially preferred.

Preferred operator sequences include, but are not limited to, tetracycline responsive element (TRE; SEQ ID NO:5; Gossen et al., Proc. Natl. Acad. Sci. 89(12):5547–5551 (1992)), LexA, Gal 4 binding sites, p53 binding sites, etc.

Thus, the operator functions essentially as an activated or inducible promoter, wherein activation comprises the presence of a sufficiently strong interaction of the bait and test protein to cause localization of the transcriptional activator domain at the operator site.

In a preferred embodiment, the operator can activate transcription bidirectionally so that both reporter genes can be placed on the same vector. That is, when the operator is used to activate more than one gene, the operator is preferably positioned between the minimal promoters controlling the expression of the reporter genes, i.e. between the coding region for a detectable gene and the coding region for a viral replication protein, if present. Alternatively, in another embodiment, the coding region for the two genes is present in an operon motif, with the single operator driving transcription of a single message containing more than one gene.

The reporter vector further comprises at least one detectable gene, which is transcribed upon activation of the operator, due to a protein—protein interaction of the bait and test proteins. By "detectable gene" herein is meant a gene whose expression results in a detectable phenotype, either by itself or with the addition of a compound or substance which results in a detectable phenotype. Suitable detectable proteins include, but are not limited to, green fluorescent protein and derivatives, luciferase, alkaline phosphatase, chloramphenicol acetyl transferase, lacZ, and drug selection genes (preferably other than those on the bait and test vectors may also be used).

In a preferred embodiment, the expression of the detectable gene allows for cell sorting, such as by fluorescence-activated cell sorting, or FACS.

In a preferred embodiment, the reporter vector comprises a viral replication protein gene. Upon activation of the operon, transcription of a viral replication protein gene results in a viral replication protein which can then bind to the viral origin of replication, causing replication of the vectors containing the origin of replication. This functions to provide a second reporter to reduce the background or "false positives", particularly when the test and bait vectors comprise selectable marker genes, since the absence of vector replication will result in cell death. Suitable viral proteins are outlined above.

In some embodiments, for example when retroviral bait and test vectors are used, the reporter vector does not need a viral replication protein gene, as retroviral vectors integrate into the host chromosome.

The compositions of the invention may be packaged into kits, or transformed into cells to detect protein—protein interactions.

In a preferred embodiment, bait and test vectors comprising cloning sites for the insertion of bait and test proteins are included in kits useful in the detection of protein—protein interactions in mammalian host cells. The kits may also include the reporter vector, or mammalian host cells as outlined herein. In a preferred embodiment, the host cell already contains at least the reporter vector, preferably integrated. In one embodiment, the kit comprises a container or receptacle with single or multiple aliquots of the bait, test and reporter vectors. Other compounds, buffers, enzymes, or reagents may also be included in the kit. The kit may have additional packaging or compounds such as tubes, beakers, holders, pipettes, buffers, salts, acids or bases. The kit may also include materials for polyacrylamide or agarose gels, as well as materials for detecting labels, if used. In some embodiments, the kit contains primers, templates or both.

In a preferred embodiment, the compositions are introduced into mammalian host cells to screen for protein—protein interactions. By "introduced into" or grammatical equivalents herein is meant that the nucleic acids enter the cells in a manner suitable for subsequent expression of the nucleic acid. The method of introduction is largely dictated by the targeted cell type and the composition of the vector. Exemplary methods include $CaPO_4$ precipitation, liposome fusion, lipofectin®, electroporation, viral infection, etc. The vectors may stably integrate into the genome of the host cell (for example, with retroviral introduction, outlined herein), or may exist either transiently or stably in the cytoplasm (i.e. through the use of traditional plasmids, utilizing standard regulatory sequences, selection markers, etc.).

As will be appreciated by those in the art, the type of cells used in the present invention can vary widely. Basically, any mammalian cells may be used, with mouse, rat, primate and human cells being particularly preferred. Accordingly, suitable cell types include, but are not limited to, tumor cells of all types particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH 3T3 cells, CHO, Cos, etc. See the ATCC cell line catalog, hereby expressly incorporated by reference.

In one embodiment, the cells may be genetically engineered, that is, contain exogenous nucleic acid in addition to the vectors of the invention.

The vectors can be introduced simultaneously, or sequentially in any order. In a preferred embodiment, host cells containing the reporter construct are generated first, and preferably the reporter vector is integrated into the genome of the host cell, for example, using a retroviral reporter vector. In a preferred embodiment, the bait vector may be integrated as well. To this end, the bait and reporter vectors may be contained on a single construct Once the components of the system are in the host cell, the cell is subjected to conditions under which the selectable markers and fusion proteins are expressed. If a test protein has sufficient affinity to the bait protein to activate transcription, the viral replication protein and the detectable protein is produced, and cells containing these proteins will survive drug selection and can be detected as outlined above. The detectable protein will be produced at a measurably higher level than in the absence of a protein—protein interaction. Thus the determination of a protein—protein interaction is generally done on the basis of the presence or absence of the detectable gene(s). Preferably positive controls comprising proteins known to associate with the bait protein are run, as well as negative controls comprising proteins known not to associate with the bait protein.

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, drug selection, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes; changes in fluorescent characteristics, etc. The preferred isolation techniques are drug selection and FACS based on the expression of the detectable gene, with a preferred embodiment utilizing both simultaneously.

Once a cell with a protein—protein interaction is detected and isolated, it is generally desirable to identify the test protein (and the bait protein, if its identity was unknown). In a preferred embodiment, the test protein nucleic acid and/or the test protein is isolated from the positive cell. This may be done in a number of ways. In a preferred embodiment, primers complementary to DNA regions common to the vector, or to specific components of the library such as a rescue sequence, defined above, are used to "rescue" the unique test sequence. Alternatively, the test protein is isolated using a rescue sequence. Thus, for example, rescue sequences comprising epitope tags or purification sequences may be used to pull out the test protein, using immunoprecipitation or affinity columns. In some instances, as is outlined below, this may also pull out the bait protein, if there is a sufficiently strong binding interaction between them. Alternatively, the test protein may be detected using mass spectroscopy.

Once rescued, the sequence of the test protein and/or test nucleic acid is determined. This information can then be used in a number of ways.

In a preferred embodiment, the test protein is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, either the test protein or the nucleic acid encoding it is used to identify other target molecules, i.e. the initially identified test protein is then used as a bait protein. It is also possible to synthetically prepare labeled proteins and use them to screen a cDNA library expressed in bacteriophage for those cDNAs which bind the protein.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Plasmid Construction

Reporter Vector

Figure 1:
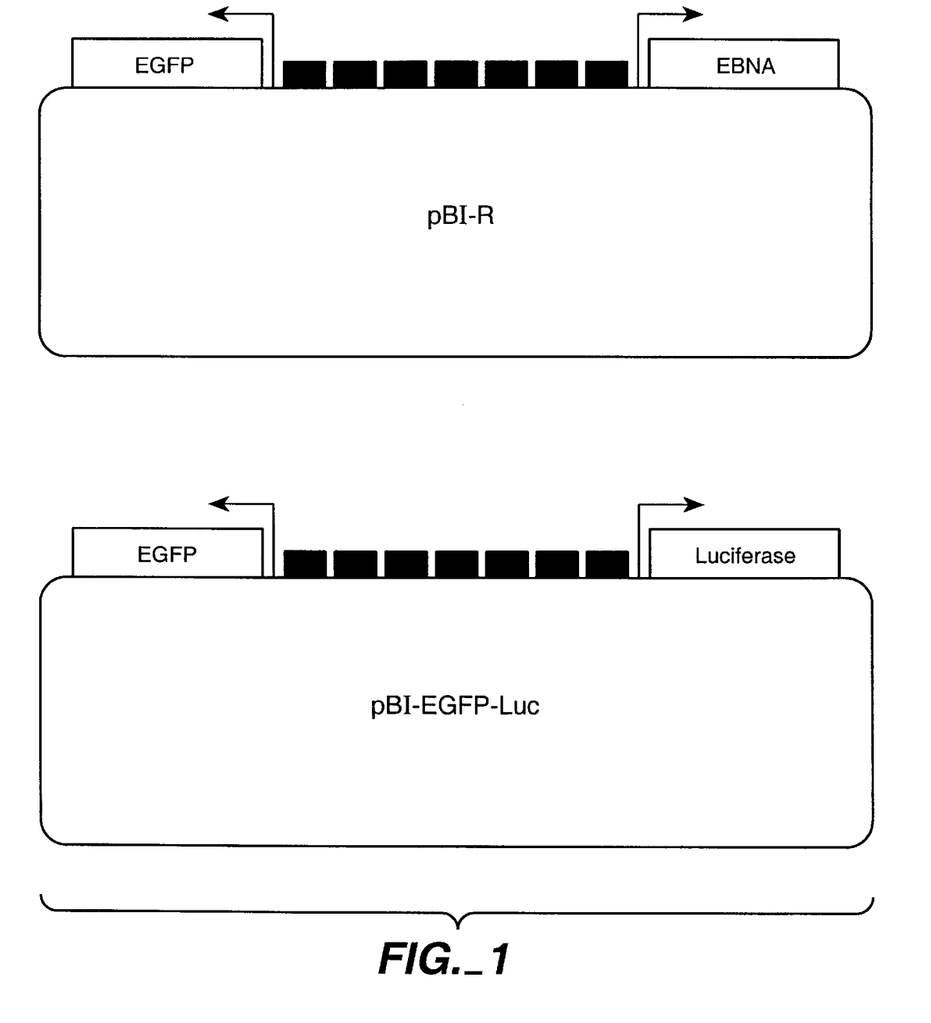
FIG. 1 depicts two reporter vectors as described in the Example.

Full length EBNA gene coding region was amplified by polymerase chain reaction from plasmid pCEP4, purchased from Invitrogen. The EBNA fragment was then cloned into pCR2. 1. Plasmid pBI-EGFP was purchased from Clontech. The EBNA fragment was transferred from pCR2.1 vector into Mlu I-Nhe I gap of pBI-EGFP to construct pBI-R, the bi-directional double reporter vector. A control vector pBI-EGFP-Luc was also purchased from Clontech with pBI-EGFP. This vector was used in quantitative luciferase assay. The test and bait vectors were made in a similar manner, as will be appreciated by those in the art. Vector maps were shown in FIG. 1.

Cell Culture and Transfection

Figure 2:
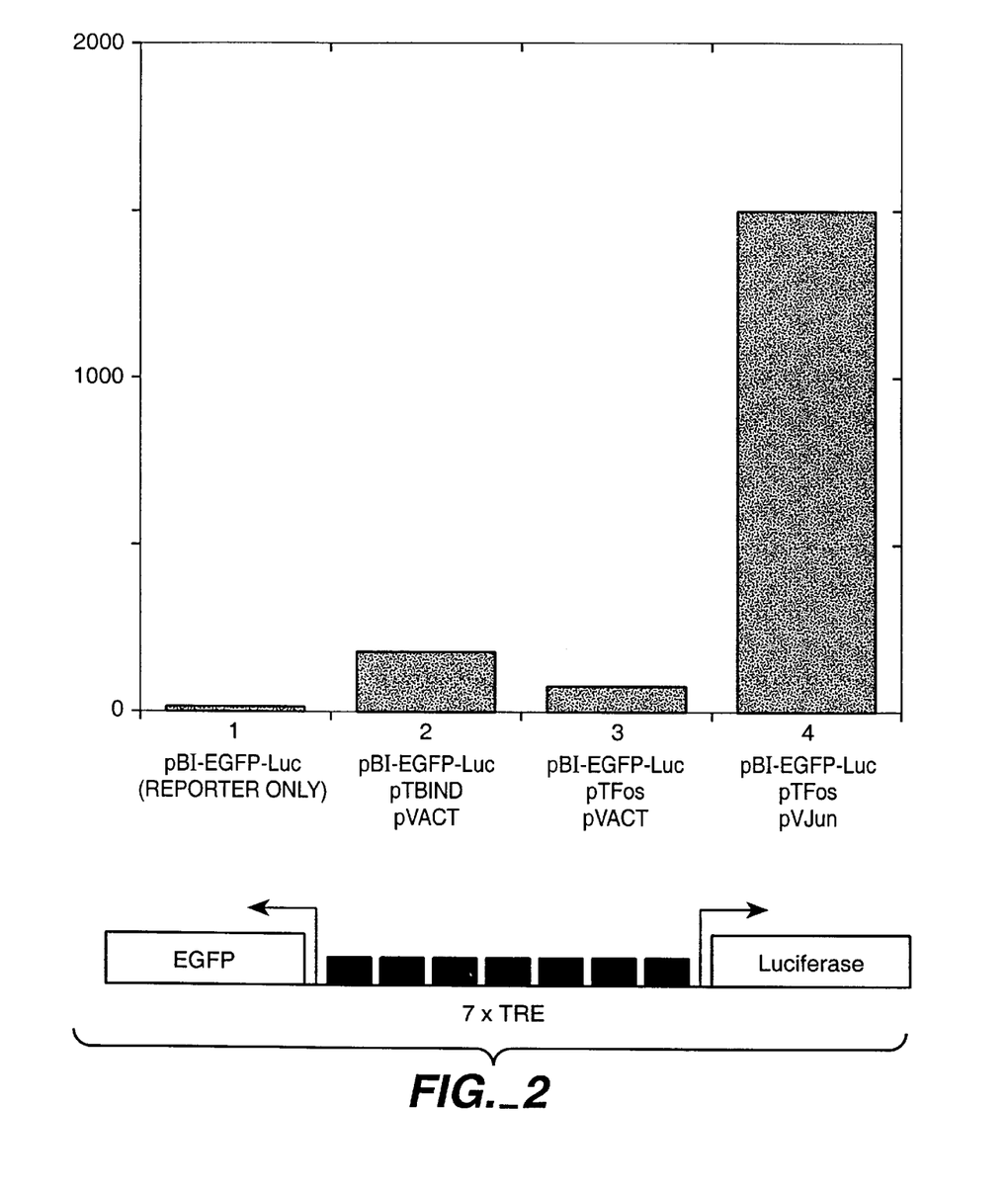
FIG. 2 depicts the identification of JUN/FOS interactions using the methods and compositions of the invention. The Y axis depicts luciferase activity.
Figure 3:
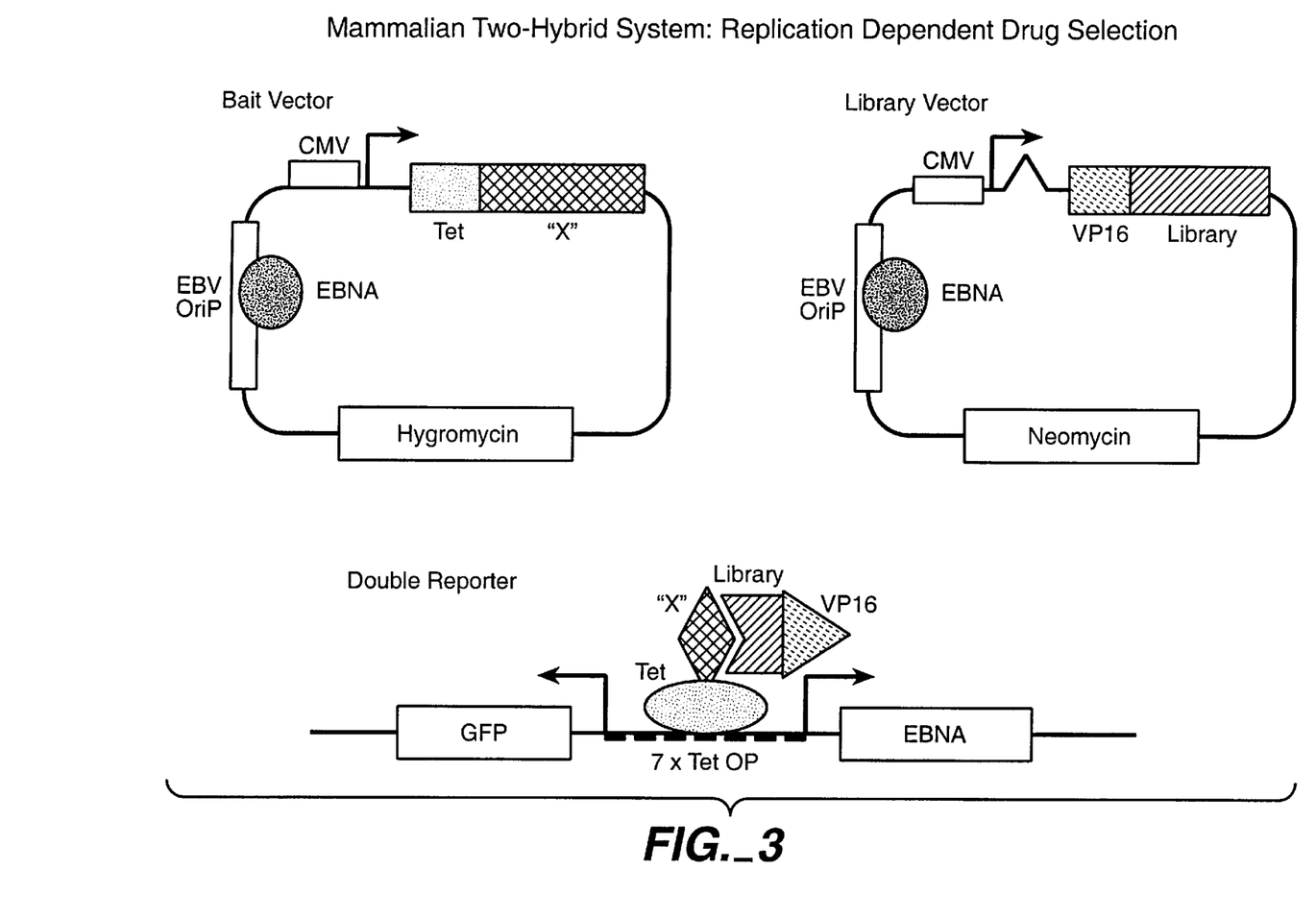
FIG. 3 depicts a preferred embodiment of the present invention.
Figure 4:
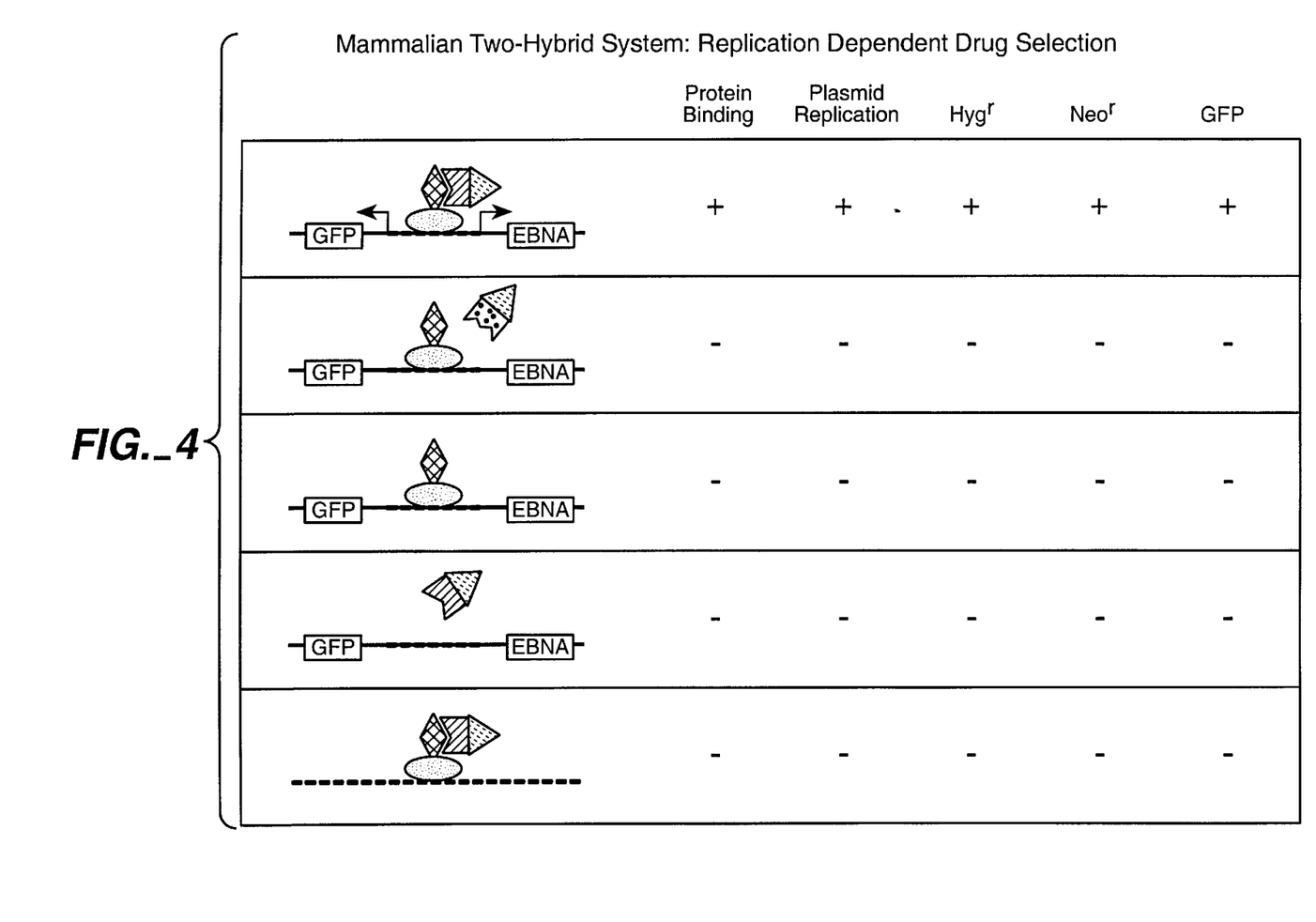
FIG. 4 schematically depicts the requirements and results of the system.

Phoenix (293 origin; see PCT/US97/01019, hereby incorporated expressly by reference in its entireity) cells were used in all of the transient assays; however, as will be appreciated, integrated reporter constructs can be made and are generally preferable. Cells were grown up in DMEM plus 10% fetal bovine serum. Plasmids were co-transfected into cells by $Ca^{2+}$ transfection method. GFP fluorescence was visible 20 hours after transfection. In FIG. 2, pCI-neo was used to balance total DNA used in control transfection. pTBIND is a vector expression a Tet DNA binding domain only. pVACT is a vector expression VP16 activation domain only. pTFOS is a vector expressing Tet-FOS fusion protein. pVJUN is a vector expression VP16-JUN fusion protein. All of the above expression vectors use CMV promoters. 3 µg of pTBIND, or pTFOS, or pVACT or pVJUN was used in transfection of each 10 cm plate as indicated in FIG. 2 (Bars). 0.5 µg of pBI-EGFP-Luc was used in transfection of a 10 cm plate for luciferase assay. 0.5 µg of pBI-R was used in GFP color assay (Pictures). Luciferase assay was done 40 hours after transfection using Promega luciferase assay kit and a Victor 1420 multilabel counter (Wallac).

Column 1 is the reporter vector pBIR only. Column 2 is the reporter vector plus the bait vector pTBIND and the test vector pVACT. Column 3 is pTFOS, pVACT and the reporter vector. Column 4 is pTFOS and pVACT and the reporter vector, co-transfected. Only column 4 shows significant luciferase activity above background, which indicates FOS/JUN interaction detected by the mammalian protein interaction cloning system.

We claim:

1. A composition comprising:

a) a bait vector comprising:

i) a first selection gene;

ii) a bait vector viral origin of replication which requires a bound viral replication protein to effect replication; and iii) a first fusion gene comprising:

1) a first sequence encoding a nucleic acid binding domain; and
2) a second sequence encoding a bait protein; and
b) a test vector comprising:
i) a second selection gene;
ii) a test vector viral origin of replication which requires a bound viral replication protein to effect replication; and
iii) a second fusion gene comprising:
1) a third sequence encoding a transcriptional activation domain; and
2) a fourth sequence encoding a test protein.

2. A composition comprising:
a) a bait vector comprising:
i) a first selection gene;
ii) a bait vector viral origin of replication which requires a bound viral replication protein to effect replication; and
iii) a first fusion gene comprising:
1) a first sequence encoding a nucleic acid binding domain; and
2) a cloning sequence comprising at least one cloning site for insertion of a nucleic acid sequence encoding a bait protein; and
b) a test vector comprising:
i) a second selection gene;
ii) a test vector viral origin of replication which requires a bound viral replication protein to effect replication; and
iii) a second fusion gene comprising:
1) a third sequence encoding a transcriptional activation domain; and
2) a cloning sequence comprising at least one cloning site for insertion of a nucleic acid sequence encoding a test protein.

3. A composition according to claims 1 or 2, further comprising:
c) a reporter vector comprising:
i) a first detectable gene;
ii) a gene encoding a viral replication protein that binds to said viral origin of replication; and
iii) an operator site, to which said nucleic acid binding domain binds.

4. A composition according to claim 1, wherein at least one of said second sequence or said fourth sequence is obtained from a library of test protein sequences.

5. A composition according to claim 1, wherein at least one of said second sequence or said fourth sequence is obtained from genomic DNA.

6. A composition according to claim 1, wherein at least one of said second sequence or said fourth sequence is obtained from cDNA.

7. A composition according to claim 1, wherein at least one of said second sequence or said fourth sequence is a random nucleic acid sequence.

8. A mammalian host cell comprising the composition of claim 1.

9. A mammalian host cell comprising the composition of claim 3.

10. A mammalian host cell according to claim 9, wherein said reporter vector is integrated into the chromosome of said host cell.

11. A mammalian host cell according to claim 9, wherein said bait vector is integrated into the chromosome of said host cell.

12. A mammalian host cell according to claim 9, wherein said test vector is integrated into the chromosome of said host cell.

13. A composition according to claim 2, wherein at least one of said test vector or said bait vector is a retroviral vector.

14. A composition comprising:
a) a retroviral bait vector comprising a first fusion gene comprising:
i) a first sequence encoding a nucleic acid binding domain; and
ii) a second sequence encoding a bait protein; and
b) a retroviral test vector comprising a second fusion gene comprising:
i) a third sequence encoding a transcriptional activation domain; and
ii) a fourth sequence encoding a test protein.

15. A composition according to claim 14, further comprising:
c) a retroviral reporter vector comprising:
i) a first detectable gene; and
ii) an operator site, to which said nucleic acid binding domain binds.

16. A composition according to claim 14, wherein said retroviral bait vector further comprises a selection gene.

17. A composition according to claim 14, wherein said retroviral test vector further comprises a selection gene.

18. A composition according to claim 14, wherein at least one of said second sequence or said fourth sequence is obtained from a library of test protein sequences.

19. A composition according to claim 14, wherein at least one of said second sequence or said fourth sequence is obtained from genomic DNA.

20. A composition according to claim 14, wherein at least one of said second sequence or said fourth sequence is obtained from cDNA.

21. A composition according to claim 14, wherein at least one of said second sequence or said fourth sequence is a random nucleic acid sequence.

22. A mammalian host cell comprising the composition of claim 14.

23. A mammalian host cell comprising the composition of claim 15.

24. A mammalian host cell according to claim 23, wherein said retroviral reporter vector is integrated into the chromosome of said host cell.

25. A mammalian host cell according to claim 23, wherein said retroviral bait vector is integrated into the chromosome of said host cell.

26. A mammalian host cell according to claim 23, wherein said retroviral test vector is integrated into the chromosome of said host cell.

27. A composition comprising:
a) a retroviral bait vector comprising a first fusion gene comprising:
i) a first sequence encoding a nucleic acid binding domain; and
ii) a cloning sequence comprising at least one cloning site for insertion of a nucleic acid sequence encoding a bait protein; and
b) a retroviral test vector comprising a second fusion gene comprising:
i) a third sequence encoding a nucleic acid binding domain; and
ii) a cloning sequence comprising at least one cloning site for insertion of a nucleic acid sequence encoding a test protein.

28. A method for detecting an interaction between a bait protein and a test protein comprising:

a) providing a mammalian host cell comprising:
  i) a bait vector comprising:
    1) a first selection gene;
    2) a bait vector viral origin of replication which requires a bound viral replication protein to effect replication; and
    3) a first fusion gene comprising:
      A) a first sequence encoding a nucleic acid binding domain; and
      B) a second sequence encoding a bait protein; and
  ii) a test vector comprising:
    1) a second selection gene;
    2) a test vector viral origin of replication which requires a bound viral replication protein to effect replication; and
    3) a second fusion gene comprising:
      A) a third sequence encoding a transcriptional activation domain; and
      B) a fourth sequence encoding a test protein; and
  iii) a reporter vector comprising:
    1) a first detectable gene;
    2) a gene encoding a viral replication protein that binds to said viral origin of replication; and
    3) an operator site, to which said nucleic acid binding domain binds; and
b) subjecting the host cell to conditions under which the first fusion gene and the second fusion gene are expressed to produce a first fusion protein and a second fusion protein; and
c) determining whether a protein—protein interaction between said first fusion protein and said second fusion protein occurred.

29. A method for detecting an interaction between a bait protein and a test protein comprising:
a) providing a mammalian host cell comprising:
  i) a retroviral bait vector comprising a first fusion gene comprising:
    1) a first sequence encoding a nucleic acid binding domain; and
    2) a second sequence encoding a bait protein; and
  ii) a retroviral test vector comprising a second fusion gene comprising:
    1) a third sequence encoding a transcriptional activation domain; and
    2) a fourth sequence encoding a test protein; and
  iii) a retroviral reporter vector comprising:
    1) a first detectable gene; and
    2) an operator site, to which said nucleic acid binding domain binds; and
b) subjecting the host cell to conditions under which the first fusion gene and the second fusion gene are expressed to produce a first fusion protein and a second fusion protein; and
c) determining whether a protein—protein interaction between said first fusion protein and said second fusion protein occurred.

30. A method according to claims 28 or 29, further comprising transforming said cell with at least one of said bait vector, said test vector, said reporter vector, said retroviral bait vector, said retroviral test vector or said retroviral reporter vector.

31. A method according to claims 28 or 29, wherein at least one of said second sequence or said fourth sequence is obtained from a library of test protein sequences.

32. A method according to claims 28 or 29, wherein at least one of said second sequence or said fourth sequence is obtained from genomic DNA.

33. A method according to claims 28 or 29, wherein at least one of said second sequence or said fourth sequence is obtained from cDNA.

34. A method according to claims 28 or 29, wherein at least one of second sequence or said fourth sequence is a random nucleic acid sequence.

35. A method according to claim 28, further comprising integrating said reporter vector into the genome of said cell.

36. A method according to claim 29, wherein said retroviral bait vector comprises a selection gene.

37. A method according to claim 29, wherein said retroviral test vector comprises a selection gene.

38. A method according to claim 29, wherein said retroviral reporter vector comprises a selection gene.

39. A method according to claim 29, further comprising integrating said retroviral reporter vector into the genome of said cell.

40. A method according to claim 29, further comprising integrating said retroviral bait vector into the genome of said cell.

41. A method according to claim 29, further comprising integrating said retroviral test vector into the genome of said cell.

* * * * *

UNITED STATES PATENT AND TRADEMARK OFFICE
CERTIFICATE OF CORRECTION

PATENT NO. : 6,114,111
DATED : September 5, 2000
INVENTOR(S) : Ying Luo et al.

It is certified that error appears in the above-identified patent and that said Letters Patent is hereby corrected as shown below:

Column 8,
Line 18, delete "GALA" and insert -- GAL4 --.

Signed and Sealed this

Seventh Day of May, 2002

Attest:

JAMES E. ROGAN
Attesting Officer  Director of the United States Patent and Trademark Office

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1937 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO:1:

| | | | | | |
|---|---|---|---|---|---|
| GCATGCAGGA | AAAGGACAAG | CAGCGAAAAT | TCACGCCCCC | TTGGGAGGTG | GCGGCATATG | 60 |
| CAAAGGATAG | CACTCCCACT | CTACTACTGG | GTATCATATG | CTGACTGTAT | ATGCATGAGG | 120 |
| ATAGCATATG | CTACCCGGAT | ACAGATTAGG | ATAGCATATA | CTACCCAGAT | ATAGATTAGG | 180 |
| ATAGCATATG | CTACCCAGAT | ATAGATTAGG | ATAGCCTATG | CTACCCAGAT | ATAAATTAGG | 240 |
| ATAGCATATA | CTACCCAGAT | ATAGATTAGG | ATAGCATATG | CTACCCAGAT | ATAGATTAGG | 300 |
| ATAGCCTATG | CTACCCAGAT | ATAGATTAGG | ATAGCATATG | CTACCCAGAT | ATAGATTAGG | 360 |
| ATAGCATATG | CTATCCAGAT | ATTTGGGTAG | TATATGCTAC | CCAGATATAA | ATTAGGATAG | 420 |
| CATATACTAC | CCTAATCTCT | ATTAGGATAG | CATATGCTAC | CCGGATACAG | ATTAGGATAG | 480 |
| CATATACTAC | CCAGATATAG | ATTAGGATAG | CATATGCTAC | CCAGATATAG | ATTAGGATAG | 540 |
| CCTATGCTAC | CCAGATATAA | ATTAGGATAG | CATATACTAC | CCAGATATAG | ATTAGGATAG | 600 |
| CATATGCTAC | CCAGATATAG | ATTAGGATAG | CCTATGCTAC | CCAGATATAG | ATTAGGATAG | 660 |
| CATATGCTAT | CCAGATATTT | GGGTAGTATA | TGCTACCCAT | GGCAACATTA | GCCCACCGTG | 720 |
| CTCTCAGCGA | CCTCGTGAAT | ATGAGGACCA | ACAACCCTGT | GCTTGGCGCT | CAGGCGCAAG | 780 |
| TGTGTGTAAT | TTGTCCTCCA | GATCGCAGCA | ATCGCGCCCC | TATCTTGGCC | CGCCCACCTA | 840 |
| CTTATGCAGG | TATTCCCCGG | GGTGCCATTA | GTGGTTTTGT | GGGCAAGTGG | TTTGACCGCA | 900 |
| GTGGTTAGCG | GGGTTACAAT | CAGCCAAGTT | ATTACACCCT | TATTTTACAG | TCCAAAACCG | 960 |
| CAGGGCGGCG | TGTGGGGGCT | GACGCGTGCC | CCCACTCCAC | AATTTCAAAA | AAAAGAGTGG | 1020 |
| CCACTTGTCT | TTGTTTATGG | GCCCCATTGG | CGTGGAGCCC | CGTTTAATTT | TCGGGGGTGT | 1080 |
| TAGAGACAAC | CAGTGGAGTC | CGCTGCTGTC | GGCGTCCACT | CTCTTTCCCC | TTGTTACAAA | 1140 |
| TAGAGTGTAA | CAACATGGTT | CACCTGTCTT | GGTCCCTGCC | TGGGACACAT | CTTAATAACC | 1200 |
| CCAGTATCAT | ATTGCACTAG | GATTATGTGT | TGCCCATAGC | CATAAATTCG | TGTGAGATGG | 1260 |
| ACATCCAGTC | TTTACGGCTT | GTCCCCACCC | CATGGATTTC | TATTGTTAAA | GATATTCAGA | 1320 |
| ATGTTTCATT | CCTACACTAG | TATTTATTGC | CCAAGGGGTT | TGTGAGGGTT | ATATTGGTGT | 1380 |
| CATAGCACAA | TGCCACCACT | GAACCCCCCG | TCCAAATTTT | ATTCTGGGGG | CGTCACCTGA | 1440 |
| AACCTTGTTT | TCGAGCACCT | CACATACACC | TTACTGTTCA | CAACTCAGCA | GTTATTCTAT | 1500 |
| TAGCTAAACG | AAGGAGAATG | AAGAAGCAGG | CGAAGATTCA | GGAGAGTTCA | CTGCCCGCTC | 1560 |
| CTTGATCTTC | AGCCACTGCC | CTTGTGACTA | AAATGGTTCA | CTACCCTCGT | GGAATCCTGA | 1620 |
| CCCCATGTAA | ATAAAACCGT | GACAGCTCAT | GGGGTGGGAG | ATATCGCTGT | TCCTTAGGAC | 1680 |
| CCTTTTACTA | ACCCTAATTC | GATAGCATAT | GCTTCCCGTT | GGGTAACATA | TGCTATTGAA | 1740 |
| TTAGGGTTAG | TCTGGATAGT | ATATACTACT | ACCCGGGAAG | CATATGCTAC | CCGTTTAGGG | 1800 |
| TTAACAAGGG | GGCCTTATAA | ACACTATTGC | TAATGCCCTC | TTGAGGGTCC | GCTTATCGGT | 1860 |
| AGCTACACAG | GCCCCTCTGA | TTGACGTTGG | TGTAGCCTCC | CGTAGTCTTC | CTGGGCCCCT | 1920 |
| GGGAGGTACA | TGTCCCC | | | | | 1937 |

(2) INFORMATION FOR SEQ ID NO:2:

(i) SEQUENCE CHARACTERISTICS:
        (A) LENGTH: 2580 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:2:

| | | | | | |
|---|---|---|---|---|---|
| ATCCTCACAG | GCCGCACCCA | GCTTTTCTTC | CGTTGCCCCA | GTAGCATCTC | TGTCTGGTGA | 60
| CCTTGAAGAG | GAAGAGGAGG | GGTCCCGAGA | ATCCCCATCC | CTACCGTCCA | GCAAAAAGGG | 120
| GGACGAGGAA | TTTGAGGCCT | GGCTTGAGGC | TCAGGACGCA | AATCTTGAGG | ATGTTCAGCG | 180
| GGAGTTTTCC | GGGCTGCGAG | TAATTGGTGA | TGAGGACGAG | GATGGTTCGG | AGGATGGGGA | 240
| ATTTTCAGAC | CTGGATCTGT | CTGACAGCGA | CCATGAAGGG | GATGAGGGTG | GGGGGGCTGT | 300
| TGGAGGGGGC | AGGAGTCTGC | ACTCCCTGTA | TTCACTGAGC | GTCGTCTAAT | AAAGATGTCT | 360
| ATTGATCTCT | TTTAGTGTGA | ATCATGTCTG | ACGAGGGGCC | AGGTACAGGA | CCTGGAAATG | 420
| GCCTAGGAGA | GAAGGGAGAC | ACATCTGGAC | CAGAAGGCTC | CGGCGGCAGT | GGACCTCAAA | 480
| GAAGAGGGGG | TGATAACCAT | GGACGAGGAC | GGGGAAGAGG | ACGAGGACGA | GGAGGCGGAA | 540
| GACCAGGAGC | CCCGGGCGGC | TCAGGATCAG | GGCCAAGACA | TAGAGATGGT | GTCCGGAGAC | 600
| CCCAAAAACG | TCCAAGTTGC | ATTGGCTGCA | AAGGGACCCA | CGGTGGAACA | GGAGCAGGAG | 660
| CAGGAGCGGG | AGGGGCAGGA | GCAGGAGGGG | CAGGAGCAGG | AGGAGGGGCA | GGAGCAGGAG | 720
| GAGGGGCAGG | AGGGGCAGGA | GGGGCAGGAG | GGCAGGAGC | AGGAGGAGGG | GCAGGAGCAG | 780
| GAGGAGGGGC | AGGAGGGGCA | GGAGGGGCAG | GAGCAGGAGG | AGGGGCAGGA | GCAGGAGGAG | 840
| GGGCAGGAGG | GGCAGGAGCA | GGAGGAGGGG | CAGGAGGGGC | AGGAGGGGCA | GGAGCAGGAG | 900
| GAGGGGCAGG | AGCAGGAGGA | GGGGCAGGAG | GGCAGGAGC | AGGAGGAGGG | GCAGGAGGGG | 960
| CAGGAGGGGC | AGGAGCAGGA | GGAGGGGCAG | GAGCAGGAGG | GGCAGGAGGG | GCAGGAGGGG | 1020
| CAGGAGCAGG | AGGGGCAGGA | GCAGGAGGAG | GGGCAGGAGG | GGCAGGAGGG | GCAGGAGCAG | 1080
| GAGGGGCAGG | AGCAGGAGGG | GCAGGAGCAG | GAGGGGCAGG | AGCAGGAGGG | GCAGGAGGGG | 1140
| CAGGAGCAGG | AGGGGCAGGA | GGGGCAGGAG | CAGGAGGGGC | AGGAGGGGCA | GGAGCAGGAG | 1200
| GAGGGGCAGG | AGGGGCAGGA | GCAGGAGGAG | GGGCAGGAGG | GGCAGGAGCA | GGAGGGGCAG | 1260
| GAGGGGCAGG | AGCAGGAGGG | GCAGGAGGGG | CAGGAGCAGG | AGGGGCAGGA | GGGGCAGGAG | 1320
| CAGGAGGAGG | GGCAGGAGCA | GGAGGGGCAG | GAGCAGGAGG | TGGAGGCCGG | GGTCGAGGAG | 1380
| GCAGTGGAGG | CCGGGGTCGA | GGAGGTAGTG | GAGGCCGGGG | TCGAGGAGGT | AGTGGAGGCC | 1440
| GCCGGGGTAG | AGGACGTGAA | AGAGCCAGGG | GGGGAAGTCG | TGAAAGAGCC | AGGGGGAGAG | 1500
| GTCGTGGACG | TGGAGAAAAG | AGGCCCAGGA | GTCCCAGTAG | TCAGTCATCA | TCATCCGGGT | 1560
| CTCCACCGCG | CAGGCCCCCT | CCAGGTAGAA | GGCCATTTTT | CCACCCTGTA | GGGGAAGCCG | 1620
| ATTATTTTGA | ATACCACCAA | GAAGGTGGCC | CAGATGGTGA | GCCTGACGTG | CCCCCGGGAG | 1680
| CGATAGAGCA | GGGCCCCGCA | GATGACCCAG | GAGAAGGCCC | AAGCACTGGA | CCCCGGGGTC | 1740
| AGGGTGATGG | AGGCAGGCGC | AAAAAAGGAG | GGTGGTTTGG | AAAGCATCGT | GGTCAAGGAG | 1800
| GTTCCAACCC | GAAATTTGAG | AACATTGCAG | AAGGTTTAAG | AGCTCTCCTG | GCTAGGAGTC | 1860
| ACGTAGAAAG | GACTACCGAC | GAAGGAACTT | GGGTCGCCGG | TGTGTTCGTA | TATGGAGGTA | 1920
| GTAAGACCTC | CCTTTACAAC | CTAAGGCGAG | GAACTGCCCT | TGCTATTCCA | CAATGTCGTC | 1980
| TTACACCATT | GAGTCGTCTC | CCCTTTGGAA | TGGCCCCTGG | ACCCGGCCCA | CAACCTGGCC | 2040
| CGCTAAGGAG | TCCATTGTCT | GTTATTTCAT | GGTCTTTTTA | CAAACTCATA | TATTTGCTGA | 2100
| GGTTTTGAAG | GATGCGATTA | AGGACCTTGT | TATGACAAAG | CCCGCTCCTA | CCTGCAATAT | 2160
| CAGGGTGACT | GTGTGCAGCT | TTGACGATGG | AGTAGATTTG | CCTCCCTGGT | TTCCACCTAT | 2220

```
GGTGGAAGGG GCTGCCGCGG AGGGTGATGA CGGAGATGAC GGAGATGAAG GAGGTGATGG      2280

AGATGAGGGT GAGGAAGGGC AGGAGTGATG TAACTTGTTA GGAGACGCCC TCAATCGTAT      2340

TAAAAGCCGT GTATTCCCCC GCACTAAAGA ATAAATCCCC AGTAGACATC ATGCGTGCTG      2400

TTGGTGTATT TCTGGCCATC TGTCTTGTCA CCATTTTCGT CCTCCCAACA TGGGGCAATT      2460

GGGCATACCC ATGTTGTCAC GTCACTCAGC TCCGCGCTCA ACACCTTCTC GCGTTGGAAA      2520

ACATTAGCGA CATTTACCTG GTGAGCAATC AGACATGCGA CGGCTTTAGC CTGGCCTCCT     2580

(2) INFORMATION FOR SEQ ID NO:3:

(i) SEQUENCE CHARACTERISTICS:
            (A) LENGTH: 66 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO:3:

AATTTTTTTT ATTTATGCAG AGGCCGAGGC CGCCTCGGCC TCTGAGCTAT TCCAGAAGTA       60

GTGAGG                                                                 66

(2) INFORMATION FOR SEQ ID NO:4:

(i) SEQUENCE CHARACTERISTICS:
            (A) LENGTH: 2479 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO:4:

TTATGTTTCA GGTTCAGGGG GAGGTGTGGG AGGTTTTTTA AAGCAAGTAA AACCTCTACA       60

AATGTGGTAT GGCTGATTAT GATCATGAAC AGACTGTGAG GACTGAGGGG CCTGAAATGA      120

GCCTTGGGAC TGTGAATCAA TGCCTGTTTC ATGCCCTGAG TCTTCCATGT TCTTCTCCCC      180

ACCATCTTCA TTTTTATCAG CATTTTCCTG GCTGTCTTCA TCATCATCAT CACTGTTTCT      240

TAGCCAATCT AAAACTCCAA TTCCCATAGC CACATTAAAC TTCATTTTTT GATACACTGA      300

CAAACTAAAC TCTTTGTCCA ATCTCTCTTT CCACTCCACA ATTCTGCTCT GAATACTTTG      360

AGCAAACTCA GCCACAGGTC TGTACCAAAT TAACATAAGA AGCAAAGCAA TGCCACTTTG      420

AATTATTCTC TTTTCTAACA AAAACTCACT GCGTTCCAGG CAATGCTTTA AATAATCTTT      480

GGGCCTAAAA TCTATTTGTT TTACAAATCT GGCCTGCAGT GTTTTAGGCA CACTGTACTC      540

ATTCATGGTG ACTATTCCAG GGGGAAATAT TTGAGTTCTT TTATTTAGGT GTTTCTTTTC      600

TAAGTTTACC TTAACACTGC CATCCAAATA ATCCCTTAAA TTGTCCAGGT TATTAATTCC      660

CTGACCTGAA GGCAAATCTC TGGACTCCCC TCCAGTGCCC TTTACATCCT CAAAAACTAC      720

TAAAAACTGG TCAATAGCTA CTCCTAGCTC AAAGTTCAGC CTGTCCAAGG GCAAATTAAC      780

ATTTAAAGCT TTCCCCCCAC ATAATTCAAG CAAAGCAGCT GCTAATGTAG TTTTACCACT      840

ATCAATTGGT CCTTTAAACA GCCAGTATCT TTTTTTAGGA ATGTTGTACA CCATGCATTT      900

TAAAAAGTCA TACACCACTG AATCCATTTT GGGCAACAAA CAGTGTAGCC AAGCAACTCC      960

AGCCATCCAT TCTTCTATGT CAGCAGAGCC TGTAGAACCA AACATTATAT CCATCCTATC     1020

CAAAAGATCA TTAAATCTGT TTGTTAACAT TTGTTCTCTA GTTAATTGTA GGCTATCAAC     1080

CCGCTTTTTA GCTAAAACAG TATCAACAGC CTGTTGGCAT ATGGTTTTTT GGTTTTTGCT     1140
```

-continued

```
GTCAGCAAAT ATAGCAGCAT TTGCATAATG CTTTTCATGG TACTTATAGT GGCTGGGCTG       1200

TTCTTTTTTA ATACATTTTA AACACATTTC AAAACTGTAC TGAAATTCCA AGTACATCCC       1260

AAGCAATAAC AACACATCAT CACATTTTGT TTCCATTGCA TACTCTGTTA CAAGCTTCCA       1320

GGACACTTGT TTAGTTTCCT CTGCTTCTTC TGGATTAAAA TCATGCTCCT TTAACCCACC       1380

TGGCAAACTT TCCTCAATAA CAGAAAATGG ATCTCTAGTC AAGGCACTAT ACATCAAATA       1440

TTCCTTATTA ACCCCTTTAC AAATTAAAAA GCTAAAGGTA CACAATTTTT GAGCATAGTT       1500

ATTAATAGCA GACACTCTAT GCCTGTGTGG AGTAAGAAAA AACAGTATGT TATGATTATA       1560

ACTGTTATGC CTACTTATAA AGGTTACAGA ATATTTTTCC ATAATTTTCT TGTATAGCAG       1620

TGCAGCTTTT TCCTTTGTGG TGTAAATAGC AAAGCAAGCA AGAGTTCTAT TACTAAACAC       1680

AGCATGACTC AAAAAACTTA GCAATTCTGA AGGAAAGTCC TTGGGGTCTT CTACCTTTCT       1740

CTTCTTTTTT GGAGGAGTAG AATGTTGAGA GTCAGCAGTA GCCTCATCAT CACTAGATGG       1800

CATTTCTTCT GAGCAAAACA GGTTTTCCTC ATTAAAGGCA TTCCACCACT GCTCCCATTC       1860

ATCAGTTCCA TAGGTTGGAA TCTAAAATAC ACAAACAATT AGAATCAGTA GTTTAACACA       1920

TTATACACTT AAAAATTTTA TATTTACCTT AGAGCTTTAA ATCTCTGTAG GTAGTTTGTC       1980

CAATTATGTC ACACCACAGA AGTAAGGTTC CTTCACAAAG ATCAAGTCCA AACCACATTC       2040

TAAAGCAACG AAGCAGTAGC AATCAACCCA CACAAGTGGA TCTTTCCTGT ATAATTTTCT       2100

ATTTTCATGC TTCATCCTCA GTAAGCACAG CAAGCATATG CAGTTAGCAG ACATTTTCTT       2160

TGCACACTCA GGCCATTGTT TGCAGTACAT TGCATCAACA CCAGGATTTA AGGAAGAAGC       2220

AAATACCTCA GTTGCATCCC AGAAGCCTCC AAAGTCAGGT TGATGAGCAT ATTTTACTCC       2280

ATCTTCCATT TTCTTGTACA GAGTATTCAT TTTCTTCATT TTTTCTTCAT CTCCTCCTTT       2340

ATCAGGATGA AACTCCTTGC ATTTTTTTAA ATATGCCTTT CTCATCAGAG GAATATTCCC       2400

CCAGGCACTC CTTTCAAGAC CTAGAAGGTC CATTAGCTGC AAAGATTCCT CTCTGTTTAA       2460

AACTTTATCC ATCTTTGCA                                                    2479
```

(2) INFORMATION FOR SEQ ID NO:5:

(i) SEQUENCE CHARACTERISTICS:
        (A) LENGTH: 312 base pairs
        (B) TYPE: nucleic acid
        (C) STRANDEDNESS: unknown
        (D) TOPOLOGY: unknown     (ii) MOLECULE TYPE: DNA     (xi) SEQUENCE DESCRIPTION: SEQ ID NO:5:

```
TTTACCACTC CCTATCAGTG ATAGAGAAAA GTGAAAGTCG AGTTTACCAC TCCCTATCAG         60

TGATAGAGAA AAGTGAAAGT CGAGTTTACC ACTCCCTATC AGTGATAGAG AAAAGTGAAA        120

GTCGAGTTTA CCACTCCCTA TCAGTGATAG AGAAAAGTGA AAGTCGAGTT TACCACTCCC        180

TATCAGTGAT AGAGAAAAGT GAAAGTCGAG TTTACCACTC CCTATCAGTG ATAGAGAAAA        240

GTGAAAGTCG AGTTTACCAC TCCCTATCAG TGATAGAGAA AAGTGAAAGT CGAGCTCGGT        300

ACCCGGGTCG AG                                                            312
```